(12) United States Patent
Benneteau et al.

(10) Patent No.: US 7,148,369 B2
(45) Date of Patent: Dec. 12, 2006

(54) ORGANOSILICON COMPOUNDS, PREPARATION METHOD AND USES THEREOF

(75) Inventors: Bernard Benneteau, Talence (FR); Jamal Bousbaa, Talence (FR); Franck Choplin, Valennes (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 377 days.

(21) Appl. No.: 10/181,631

(22) PCT Filed: Jan. 17, 2001

(86) PCT No.: PCT/FR01/00139

§ 371 (c)(1),
(2), (4) Date: Nov. 12, 2002

(87) PCT Pub. No.: WO01/53303

PCT Pub. Date: Jul. 26, 2001

(65) Prior Publication Data

US 2003/0166957 A1    Sep. 4, 2003

(30) Foreign Application Priority Data

Jan. 20, 2000  (FR) ................................ 00 00695

(51) Int. Cl.
    C07F 7/04  (2006.01)
    C07F 7/10  (2006.01)
    C07F 7/08  (2006.01)

(52) U.S. Cl. .................... 556/413; 556/419; 556/427; 556/437

(58) Field of Classification Search ........... 556/413, 556/427, 437; 526/279; 428/333
    See application file for complete search history.

(56) References Cited

U.S. PATENT DOCUMENTS 5,466,486 A * 11/1995 Ogawa et al. .............. 427/352
5,876,801 A *  3/1999 Ogawa et al. .............. 427/387

FOREIGN PATENT DOCUMENTS

JP      08188448      * 7/1996

OTHER PUBLICATIONS

Borchardt et al., Body Distribution of 75Se-Radiolabeled Silica Nanoparticles Covalently Coated with a-Functionalized Surfactants after Intravenous Injection in Rats, Journal of Drug Targeting, 1994, 2 (1), 61-77.*
International PCT Patent Application No. PCT/FR01/00139, filed Jan. 17, 2001, International Publication No. WO 01/00139, published Jul. 26, 2001.

(Continued)

*Primary Examiner*—J. Parsa
*Assistant Examiner*—Chukwuma Nwaonicha
(74) *Attorney, Agent, or Firm*—Thomas W. Tolpin; Welsh & Katz, Ltd.

(57) ABSTRACT

The invention concerns organosilicon compounds, their method of preparation and their use as coupling agents for deposition, at the surface of a solid support, an organized self-assembled monolayer. The invention also concerns a method for obtaining solid supports whereof the surface is modified by an organized self-assembled monolayer comprising a system of said organosilicon compounds, and the use of said solid supports for biomolecular synthesis or immobilization.

17 Claims, 6 Drawing Sheets

OTHER PUBLICATIONS

English translation of International PCT Patent Application No. PCT/FR01/00139, filed PCT/FR01/00139, filed Jan. 17, 2001, International Publication No. WO 01/00139, published Jul. 26, 2001.

European Patent Application No. 91118078.4, filed Oct. 23, 1991, Publication No. 0 482 613 A1, published Apr. 29, 1992, of Matsushita Electric Industrial Co., Ltd, no date.

European Patent Application No. 93100300.8, filed Jan. 11, 1993, Publication No. 0 552 637 A1, published Jul. 28, 1993, of Matsushita Electric Industrial Co., Ltd.

European Patent Application No. 94114633.4, filed Jan. 21, 1992, Publication No. 0 629 673 A3, published Apr. 29, 1992, of Matsushita Electric Industrial Co., Ltd.

Abstract: Japanese Application No. 09254531 filed Sep. 19, 1997, Publication No. 11092251published Apr. 6, 1999 of Matsushita Electric Ind Co., Ltd.

Abstract: Japanese Application No. 05199579 filed Aug. 11, 1993, Publication No. 07051355 published Feb. 28, 1995 of Kuraray Co., Ltd.

* cited by examiner

10

12

13

ORGANOSILICON COMPOUNDS, PREPARATION METHOD AND USES THEREOF

CROSS REFERENCES TO RELATED APPLICATIONS

This application is based upon priority International Application PCT/FR01/00139 filed Jan. 17, 2001, International Publication No. WO 01/53303 A1 published Jul. 26, 2001, which is based upon priority French Application FR 00/00695 filed Jan. 20, 2000.

BACKGROUND OF THE INVENTION

The present invention relates to organosilicon compounds, to their process of preparation and to their use in depositing a self-assembled monolayer of these compounds at the surface of a solid support. The present invention also relates to the solid supports thus modified and to their process of preparation, in addition to their use in the synthesis or immobilization of biomolecules.

An organized self-assembled monolayer (SAM) is defined as an assemblage of molecules in which the molecules are organized, which organization is due to interactions between the chains of the molecules, giving rise to a stable, monomolecular and well-ordered anisotropic film (A. Ulman, *Chem. Rev.*, 1996, 96, 1533–1554).

These self-assembled monolayers, which can be obtained reproducibly (J. B. Brozska et al., *Langmuir*, 1994, 10, 4367–4373), have the distinguishing feature of forming a dense and homogeneous film which is resistant to chemical treatments (acidic or basic).

The formation of SAM on solid supports, for example using octadecyltrichlorosilane, makes possible the preparation of homogeneous organic surfaces with well defined parameters, both chemically and structurally. These surfaces can act as two-dimensional models for fundamental studies, in particular as regards self-assembling phenomena and the chemistry of interfaces (A. Ulman, ibid).

Various organosilicon compounds have been used as coupling agents for the functionalization of solid supports (L. A. Chrisey et al., *Nucleic Acids Research*, 1996, 24, 15, 3031–3039, U. Maskos et al., *Nucleic Acids Research*, 1992, 20, 7, 1679–1684) with the aim of immobilizing oligonucleotides or of synthesizing them in situ. However, the organosilicon coupling agents used in these studies form non-homogeneous films which have very little resistance to the subsequent chemical treatments for the synthesis or immobilization of oligonucleotides. Furthermore, the formation of the films with these coupling agents is not reproducible.

BRIEF SUMMARY OF THE INVENTION

The Inventors thus set themselves the aim of overcoming the disadvantages of the prior art and of providing for coupling agents which make it possible to obtain true SAMs at the surface of solid supports, namely stable monolayer films in which the molecules are self-assembled and organized. The Inventors also set themselves the aim of providing for coupling agents which can be reproducibly grafted to solid supports, while rendering possible syntheses or immobilizations of biomolecules at the surface of the monolayer formed on the support.

A subject matter of the present invention is organosilicon compounds of formula (I)

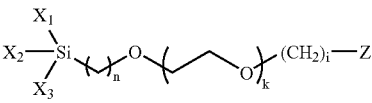

in which:
n is between 15 and 35, preferably between 20 and 25,
k is between 0 and 100, preferably between 0 and 5,
i is an integer greater than or equal to 0, preferably equal to 0 or to 1,
$X_1$, $X_2$ and $X_3$, which can be identical to or different from one another, are selected from the group consisting of saturated, linear or branched, $C_1$ to $C_6$ alkyls and hydrolyzable groups, at least one from $X_1$, $X_2$ or $X_3$ representing a hydrolyzable group, and
if k=0 and i=0, then Z represents an $R_1$ group,
if k=0 and i≧1, then Z represents an $—OR_1$, $—OCOR_1$, $—NR_1R_2$, $—COOR_1$, $—CONR_1R_2$ or $—SR_1$ group or a halogen atom,
if k≧1 and i=0, then Z represents an $—R_1$, $—COR_1$, $—COOR_1$, $—CONR_1R_2$, $—CF_3$ or $—(CF_2)_jCF_3$ group, j being between 1 and 10,
if k≧1 and i≧1, then Z represents an $—OR_1$, $—OCOR_1$, $—NR_1R_2$, $—COOR_1$, $—CONR_1R_2$, $—SR_1$, $—CF_3$ or $—(CF_2)_jCF_3$ group, j being as defined above, or a halogen atom,
$R_1$ and $R_2$, which can be identical or different, represent a hydrogen atom, an optionally substituted, saturated or unsaturated and linear or branched hydrocarbonaceous chain comprising from 1 to 24 carbon atoms, or an aromatic group, provided that, when k=i=0 and n=15, $R_1$ is other than the $—CH_2CF_3$ group and, when k=i=0 and n=19, $R_1$ is other than the $—(CH_2)_6—C≡C—C≡CH$ group.

When Z represents an $—OR_1$, $—OCOR_1$ or $—COOR_1$ group, irrespective of the values of i, and when k≧1, then it is clearly understood that Z can represent any group resulting from the protection of a hydroxyl or carboxylic acid functional group, such as the protective groups described in *Protective groups in organic synthesis* (T. W. Greene et al., 2nd edition, Wiley Interscience), for example a cyclic protective group.

Within the meaning of the present invention, the term "aromatic" is understood to mean any group which has one or more aryl rings, for example a phenyl ring. The term "hydrolyzable group" is understood to mean any group capable of reacting with an acid in an aqueous medium so as to give the compounds $X_1H$, $X_2H$ or $X_3H$.

Preferably, said hydrolyzable group is selected from the group consisting of halogen atoms, the $—N(CH_3)_2$ group and $—OR$ groups, R being a saturated, linear or branched, $C_1$ to $C_6$ alkyl group.

As regards the Z groups and the hydrolyzable groups, suitable halogen atoms are just as easily fluorine as chlorine, bromine or iodine.

The organosilicon compounds according to the present invention advantageously exhibit highly varied functionalities, in view of the diversity of the end Z groups which can be used, it being possible for these Z groups to be modified and functionalized as desired according to organic chemistry reactions well known to a person skilled in the art.

According to an advantageous embodiment, a compound of formula (I) is such that $X_1$, $X_2$ and $X_3$ represent chlorine atoms, n is equal to 22, i is equal to 0, k is equal to 1 or to 3 and Z represents a —COCH$_3$ group.

According to another advantageous embodiment, a compound of formula (I) is such that X$_1$, X$_2$ and X$_3$ represent chlorine atoms, n is equal to 22, i is equal to 1, k is equal to 2 and Z represents a —COOCH$_3$ group.

Surprisingly, the products selected indeed make it possible to obtain true SAMs at the surface of solid supports, namely stable monolayer films in which the molecules are self-assembled and organized.

Another subject matter of the present invention is a process for the preparation of the compounds of formula (I) described above in which i is other than 1, which process comprises the following stages:

a) preparation of an unsaturated precursor of formula (III)

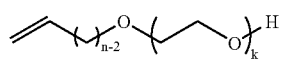

by reaction of a diol of formula HO—(CH$_2$—CH$_2$—O)$_k$—H with an unsaturated compound of formula (II):

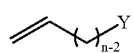

in which Y represents a nucleofuge group and n and k are as defined above in connection with the formula (I);

b) production, by functionalization of the hydroxyl end of the compound of formula (III), of an unsaturated precursor of formula (IV):

in which Z and i are as defined above in connection with the formula (I);

c) production, by hydrosilylation of the unsaturated precursor of formula (IV) using a hydrosilane of formula HSiX$_1$X$_2$X$_3$, of a silicon compound of formula (I):

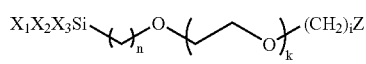

in which at least one from X$_1$, X$_2$ and X$_3$ represents a halogen atom; and d) optionally, production of another compound of formula (I) by substitution of one or more of the X$_1$, X$_2$ and X$_3$ groups of the compound obtained in stage c) using X$_1$, X$_2$ and/or X$_3$ groups as defined in connection with the compound of formula (I) according to the present invention.

Stage b) of functionalization of the hydroxyl end of the compound of formula (III) can, for example, be carried out, when i is equal to 0, by an esterification reaction using alkyl chloride when Z represents a —COR$_1$ group, R$_1$ being as defined in connection with the compound of formula (I) according to the invention.

Another subject matter of the present invention is a process for the preparation of the compounds of formula (I) according to the present invention as described above in which i is equal to 1, which process comprises the following stages:

a) preparation of an unsaturated precursor of formula (III'):

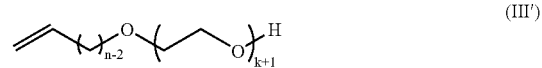

by reaction of an unsaturated compound of formula (II) as defined above with a diol of formula HO—(CH$_2$—CH$_2$—O)$_{k+1}$—H, n and k being as defined above in connection with the compound of formula (I) according to the present invention;

b) production, by oxidation of the hydroxyl end of the compound (III'), of an unsaturated precursor of formula (IV'):

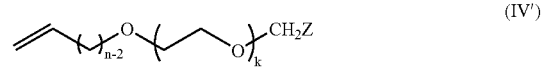

in which Z represents a carboxylic acid functional group;

c) optionally, functionalization of the carboxylic acid end of the compound of formula (IV') using another Z group as defined in connection with the formula (I) of the compounds according to the present invention;

d) production, by hydrosilylation of the unsaturated precursor of formula (IV') using a hydrosilane of formula HSiX$_1$X$_2$X$_3$, of a silicon compound of formula (I):

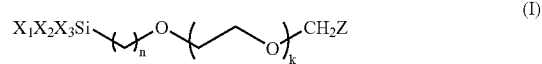

in which at least one from X$_1$, X$_2$ and X$_3$ represents a halogen atom; and e) optionally, production of another compound of formula (I) by substitution of one or more of the X$_1$, X$_2$ and X$_3$ groups of the compound obtained in stage d) using X$_1$, X$_2$ and/or X$_3$ groups as defined in connection with the compound of formula (I) according to the present invention.

In the processes described above for the preparation of the compounds of formula (I) according to the invention, whatever the value of i, stage a) is advantageously carried out in a polar solvent, for example water or tetrahydrofuran, in a basic medium and at the reflux temperature of the solvent; use may be made, as nucleofuge group Y present in the compound of formula (II), of, for example, a halogen atom or a tosyl group; furthermore, the stage of hydrosilylation of the unsaturated precursor can be carried out in the presence of trichlorosilane.

The organosilicon compounds of formula (I) according to the present invention can, for example, be used in sol-gel processes, that is to say be hydrolyzed and then crosslinked so as to obtain novel materials, or alternatively can act as comonomers in syntheses of novel polymers with the aim of modifying the chemical and mechanical properties of these polymers through the functionalities introduced, for example in the form of pendent chains. They can also be used to form an organized self-assembled monolayer at the surface of a solid support.

Thus, another subject matter of the present invention is the use of an organosilicon compound of general formula (I'):

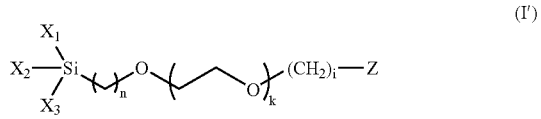

in which:
n is between 15 and 35,
k is between 0 and 100,
i is an integer greater than or equal to 0,
$X_1$, $X_2$ and $X_3$, which can be identical to or different from one another, are selected from the group consisting of saturated, linear or branched, $C_1$ to $C_6$ alkyls and hydrolyzable groups, at least one from $X_1$, $X_2$ or $X_3$ representing a hydrolyzable group, and
if k=0 and i=0, then Z represents an $R_1$ group,
if k=0 and i≧1, then Z represents an —$OR_1$, —$OCOR_1$, —$NR_1R_2$, —$COOR_1$, —$CONR_1R_2$ or —$SR_1$ group or a halogen atom,
if k≧1 and i=0, then Z represents an —$R_1$, —$COR_1$, —$COOR_1$, —$CONR_1R_2$, —$CF_3$ or —$(CF_2)_jCF_3$ group, j being between 1 and 10,
if k≧1 and i≧1, then Z represents an —$OR_1$, —$OCOR_1$, —$NR_1R_2$, —$COOR_1$, —$CONR_1R_2$, —$SR_1$, —$CF_3$ or —$(CF_2)_jCF_3$ group, j being as defined above, or a halogen atom,
$R_1$ and $R_2$, which can be identical or different, represent a hydrogen atom, an optionally substituted, saturated or unsaturated and linear or branched hydrocarbonaceous chain comprising from 1 to 24 carbon atoms, or an aromatic group, to form, at the surface of a solid support, an organized self-assembled monolayer.

The use of the organosilicon compounds of general formula (I') makes it possible to advantageously modify the surface of solid supports by a dense and organized monolayer which corresponds to the definition of the SAMs given above. The monolayer thus formed on the surface exhibits high resistance with respect to chemical treatments (acidic or basic). The robustness and homogeneity of the monolayer formed at the surface of the support by the organosilicon agents according to the present invention make it possible, for example, to treat supports against corrosion.

The compounds grafted to the support give rise to strong covalent bonds of siloxane type with the surface and develop strong cohesion between their alkyl chains, the result of a self-assembling of the molecules, which protects the siloxane bonds. In addition, the grafting is reproducible and the Z groups of the grafted compounds exhibit high chemical reactivity.

Another subject matter of the present invention is a solid support, the surface of which is modified by an organized self-assembled monolayer, characterized in that said monolayer comprises a network of at least one organosilicon compound of general formula (I') as defined above.

Within the meaning of the present invention, the term "network" is understood to mean an assemblage of molecules in which the molecules are organized and in which the chains of the molecules interact with one another via covalent bonds or noncovalent bonds (for example, Van der Waals forces).

It is clearly understood that said monolayer, in addition to the organosilicon compounds of general formula (I') according to the present invention, can also comprise any other type of compound capable of being grafted to the solid support (production of a "mixed" monolayer), which makes it possible to reduce the density of the compounds of formula (I') on the support, when such an effect is desired.

Suitable solid supports are those possessing a hydrated surface. Preferably, said solid support is such that its surface exhibits, before being modified, hydroxyl groups. It is advantageously selected from the group consisting of glasses, ceramics (preferably of oxide type), metals (for example, aluminum or gold) and semimetals (such as oxidized silicon).

Another subject matter of the present invention is a process for the production of a solid support as defined above, characterized in that it comprises the following stages:
a) removal of contaminants from a solid support and hydration and/or hydroxylation of its surface,
b) introduction, under an inert atmosphere, of at least one organosilicon compound of general formula (I') as defined above into a mixture of at least two solvents comprising at least one nonpolar hydrocarbonaceous solvent,
c) silanization of the support obtained in stage a) by immersion in the solution prepared in stage b), and
d) rinsing of the modified support obtained in stage c) using a solvent, preferably a polar solvent.

The term "contaminant" of the solid support is understood to mean any compound, such as grease, dust or other compounds, present at the surface of the support and which does not form part of the chemical structure of the support itself.

The process according to the invention makes it possible advantageously to chemically modify the properties of an inorganic surface, this being achieved as a function of the Z groups introduced by the organosilicon compounds grafted to the surface.

In a particularly advantageous way, according to the nature of the solid support, stage a) is carried out using one or more solvents and/or oxidizing agents and/or hydroxylating agents (for example, a chromium(VI)/sulfuric acid mixture), a detergent (for example, Hellmanex®), a photochemical treatment with ozone or any other appropriate treatment.

Stage b) can advantageously be carried out in a mixture of at least one nonpolar hydrocarbonaceous solvent and of at least one polar solvent. In this case, the proportions by volume of the nonpolar solvent with respect to the polar solvent are preferably between 70/30 and 95/5. By way of examples and without implied limitation, a nonpolar hydrocarbonaceous solvent which can be used is cyclohexane and a polar solvent which can be used is chloroform.

The concentration of the organosilicon compound in the mixture of solvents, in stage b) of the process according to the present invention, is advantageously between $1 \times 10^{-5}$ and $1 \times 10^{-2}$ mol/liter.

Stage c) of silanization of the support can be carried out for a time of between 1 minute and 3 days and at a temperature of between −10° C. and 120° C., according to the solvents used.

The solid supports, the surfaces of which are modified by an organized self-assembled monolayer according to the present invention, can advantageously be used, as a function of the nature of the Z terminal group, as supports for the synthesis or the immobilization of biomolecules, for example oligonucleotides or proteins.

Thus, another subject matter of the present invention is the use of a solid support as described above in the synthesis or the immobilization of biomolecules via covalent bonding.

A more particular subject matter of the present invention is a process for the synthesis of biomolecules on a solid support as described above, characterized in that said biomolecules are composed of a sequence of repeat units and in that said process comprises successive stages of grafting said repeat units, the first grafted repeat unit carrying a functional group which is reactive with respect to the Z groups of the organosilicon compounds present on the solid support.

An additional subject matter of the present invention is a process for the immobilization of biomolecules on a solid support as described above, characterized in that it comprises a stage of grafting said biomolecules, which carry functional groups which are reactive with respect to the Z groups of the organosilicon compounds, to said solid support.

Before carrying out the processes for the synthesis or immobilization of biomolecules described above, and in the case where the Z terminal functional group of the organosilicon compounds is, for example, an —$OCOR_1$ group (in which $R_1$ is as defined in connection with the formula (I') of the compounds according to the present invention) or a —$COOR_1$ group (in which $R_1$ is as defined in connection with the formula (I') of the compounds according to the present invention but is other than a hydrogen atom), the corresponding alcohol or carboxylic acid functional group can be deprotected beforehand, if necessary, by an appropriate chemical treatment, such as 0.5M potassium hydroxide in a water/ethanol mixture.

In addition to the applications which have just been mentioned above, the solid supports according to the present invention can also be used, by way of examples and without implied limitation, to graft catalysts to inorganic supports or, in the field of combinatorial chemistry, to carry out varied chemical syntheses on solid supports. They can also be subjected to subsequent chemical modifications: for example, treatment with amines of a solid support to which brominated organosilicon compounds according to the present invention are grafted makes it possible to obtain a surface with biocidal properties.

In addition to the preceding arrangements, the invention also comprises other arrangements which will emerge from the description which will follow, which description refers to examples of the synthesis of organosilicon compounds according to the present invention and of the modification of solid supports by an organized self-assembled monolayer of these organosilicon compounds, as well as to the appended drawings.

DETAILED DESCRIPTION OF THE INVENTION

A detailed description of the preferred embodiments and best modes for practicing the invention are discussed herein along with some examples thereof.

It must be clearly understood, however, that these examples are given solely by way of illustration of the subject matter of the invention, of which they do not in any way constitute a limitation.

EXAMPLE 1

Synthesis of Organosilicon Compounds of Formula (I)

Figure 1:
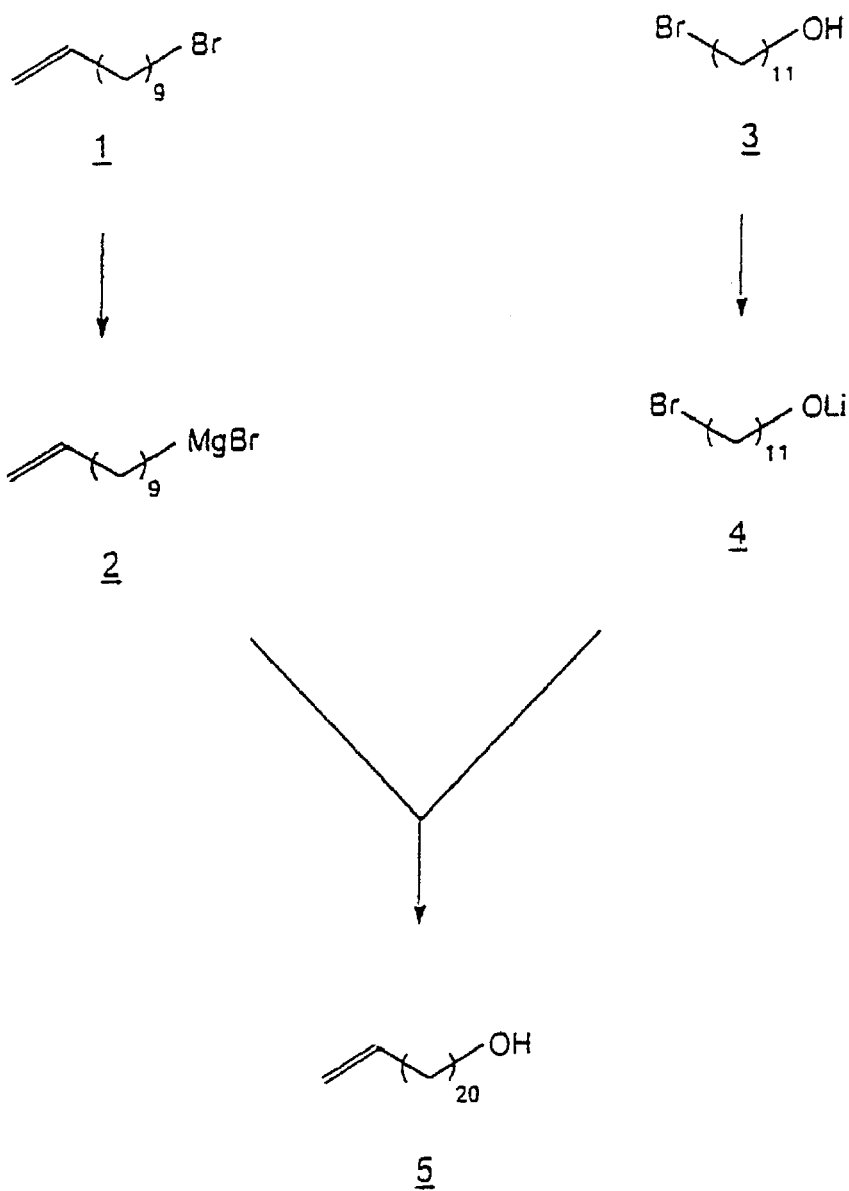
FIGS. 1, 2 and 3 illustrate the synthesis of unsaturated precursors of the organosilicon compounds according to the present invention.

1) Synthesis of an Unsaturated Alcohol (FIG. 1)

Preparation of the Magnesium Derivative 2

Magnesium (1.8 g, 70 mmol) is introduced into a 500 ml three-necked round-bottomed flask under an inert atmosphere. The unsaturated brominated derivative 1 (16.3 g, 70 mmol), dissolved beforehand in 70 ml of anhydrous THF (tetrahydrofuran), is added dropwise. A few drops of dibromoethane may be necessary to activate the magnesium. The reaction mixture is brought to reflux for 1 h 30 in order to obtain the magnesium derivative 2, which will be used immediately.

Preparation of the Lithium Alkoxide 4

The bromoalcohol 3 (17.7 g, 70 mmol, 1 eq) is dissolved in 70 ml of anhydrous THF in a dry 250 ml three-necked round-bottomed flask under an inert atmosphere. The solution is cooled to −78° C. and then methyllithium (50 ml, 80 mmol, 1.1 eq) is added dropwise. The lithium alkoxide 4 is obtained.

Preparation of the Unsaturated Alcohol 5

The magnesium derivative 2 is cooled to −78° C. and then copper iodide (1.1 g, 3.5 mmol, 0.05 eq) is added. The solution is stirred for 25 minutes at −78° C. and then reheated to ambient temperature until a crimson color is obtained. The solution is then immediately cooled to −78° C. and the lithium alkoxide 4 is introduced using a hollow needle under an argon atmosphere. The solution is stirred for 1 h at −78° C. and then for 18 h at ambient temperature. The excess methyllithium is destroyed by addition of ethanol, followed by hydrolysis in an acidic medium by addition of a 10% aqueous hydrochloric acid solution. The organic phase is extracted three times with diethyl ether. The ethereal phases are combined and washed with a 10% hydrochloric acid solution, with water and finally with a saturated aqueous $NaHCO_3$ solution. The organic phase is subsequently washed to neutrality, dried over $MgSO_4$ and then concentrated under vacuum. The product is purified by reprecipitation from acetone. The compound 5 is obtained in the form of a white solid (19.8 g; melting point of 61.7–62.8° C.; yield of 87%). Its analysis by infrared and proton and carbon-13 NMR is as follows.

IR ($\nu(cm^{-1})$): 3330, 3079, 2919, 2851, 1642

$^1$H NMR ($CDCl_3$, δ (ppm)): 6.0–5.7 (m, 1H), 5.1–4.7 (m, 2H); 3.6 (t, 2H), 2.2–1.9 (m, 2H) and 1.7–1.2 (m, 37H, including 1H exchangeable with $D_2O$).

$^{13}$C NMR (CDCl$_3$, δ (ppm)): 139.3, 113.8, 62.8, 33.6–25.8 (19 CH$_2$).

Figure 2:
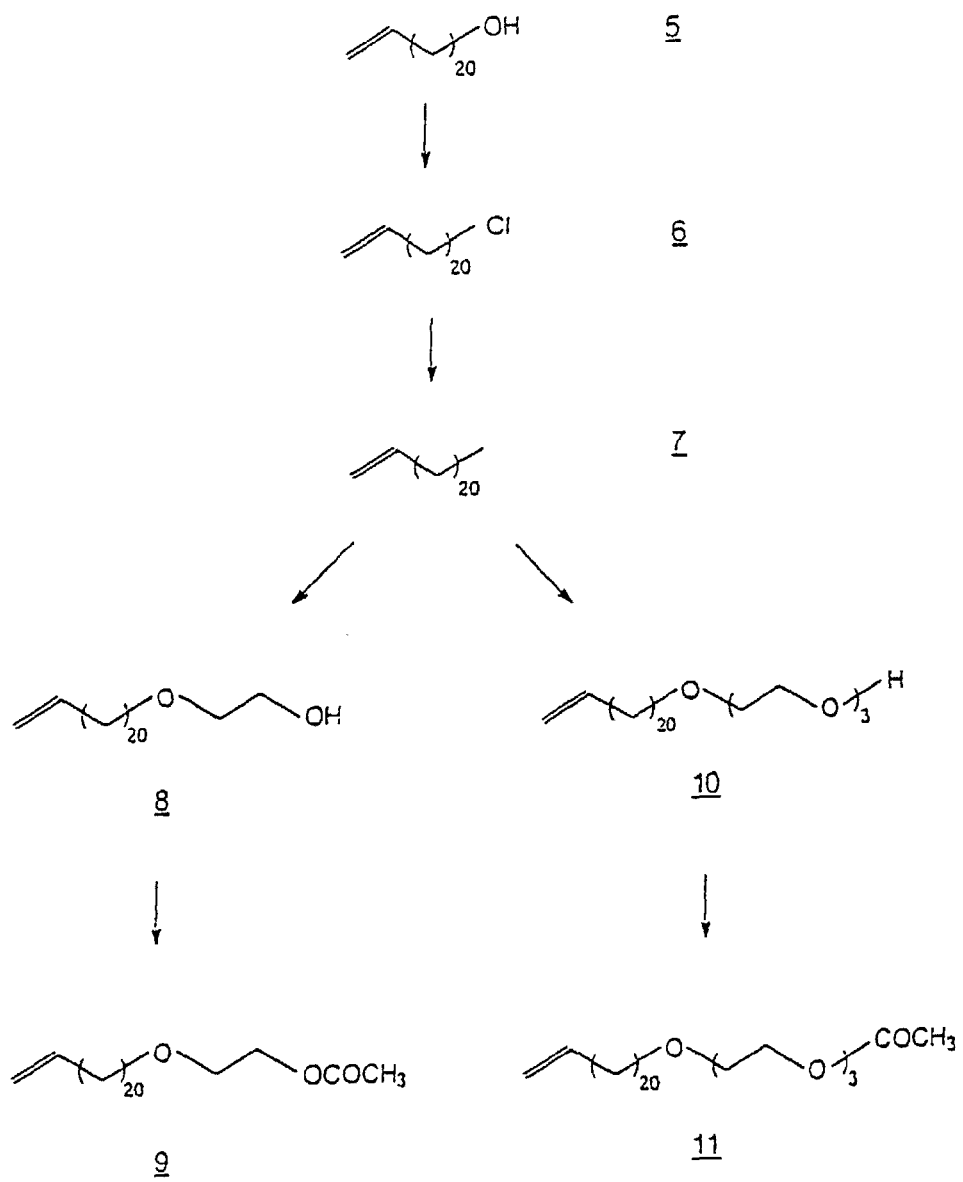

2) Introduction of an Ethylene Glycol (FIG. 2)

Synthesis of the Unsaturated Chlorinated Derivative 6

The alcohol 5 obtained above (15 g, 46 mmol, 1 eq) and pyridine (40.36 ml, 6 mmol, 0.1 eq) are introduced into a 250 ml two-necked round-bottomed flask equipped with a mechanical stirrer and surmounted by a vertical reflux condenser. Thionyl chloride (6 ml, 70 mmol, 1.5 eq) is then added dropwise. The reaction medium is stirred for 1 h and is then brought to reflux until the OH band has completely disappeared (monitored by infrared spectroscopy). The reaction medium is subsequently hydrolyzed and then extracted three times with diethyl ether. The ethereal phases are combined and washed with a 10% hydrochloric acid solution, with water and then with a saturated NaHCO$_3$ solution. The ethereal phase is subsequently washed to neutrality, dried over MgSO$_4$ and concentrated under vacuum. The compound 6 is obtained in the form of a yellow solid and is then purified by silica chromatography (eluent: petroleum ether/ether, 70/30 v/v); a white solid is obtained (14 g; melting point of 34.1–34.9° C.; yield of 75%). Its analysis by infrared and proton and carbon-13 NMR is as follows.

IR (dispersion in KBr) ν (cm$^{-1}$): 3076, 2917, 2849, 1641.
$^1$H NMR (CDCl$_3$, δ (ppm)): 6.0–5.7 (m, 1H), 5.1–4.7 (m, 2H), 3.5–3.3 (t, 2H), 2.2–1.9 (m, 2H) and 1.7–1.2 (m, 36H).
$^{13}$C NMR (CDCl$_3$, δ (ppm)): 139.2, 113.8, 33.8–25.6 (20 CH$_2$)

Synthesis of the Unsaturated Iodinated Derivative 7

The unsaturated chlorinated compound 6 (10.6 g, 32 mmol) and sodium iodide (22 g, 140 mmol, 4 eq) are dissolved in acetone (40 ml) in a 250 ml round-bottomed flask. The solution is then brought to reflux for 18 h. The reaction medium is subsequently extracted with diethyl ether and the ethereal phases are combined, then washed with water, dried over MgSO$_4$ and concentrated under vacuum. The product is purified by precipitation operations from acetone. The compound 7 is obtained in the form of a yellow solid (11 g; melting point of 41.1–42.0° C.; yield of 81%). Its analysis by infrared and proton and carbon-13 NMR is as follows.

IR (dispersion in KBr) ν (cm$^{-1}$): 3076, 2917, 2849, 1641.
$^1$H NMR (CDCl$_3$, δ (ppm)): 6.0–5.7 (m, 1H), 5.1–4.7 (m, 2H), 3.2–3.0 (t, 2H), 2.2–1.9 (m, 2H) and 1.7–1.2 (m, 36H).
$^{13}$C NMR CDCl$_3$, δ (ppm)): 139.2, 113.8, 33.8–25.6 (20 CH$_2$)

Synthesis of the Unsaturated Alcohol 8

A solution of ethylene glycol (11.5 g, 180 mmol, 10 eq) and of sodium hydroxide (3.7 g, 90 mmol, 5 eq), reduced beforehand to a powder, in 20 ml of anhydrous THF is brought to reflux for 30 minutes. The iodinated compound 7 (8 g, 18 mmol, 1 eq) and tetrabutylammonium hydrogensulfate (0.62 g, 1.8 mmol, 0.1 eq) are added. The reaction medium is subsequently brought to reflux for 72 h. After returning to ambient temperature, an aqueous hydrochloric acid solution (10%, 50 ml) is introduced. The reaction medium is subsequently extracted three times with diethyl ether; the ethereal phases are combined and washed twice with a 10% hydrochloric acid solution, with water and then with a saturated NaHCO$_3$ solution. The ethereal phase is subsequently washed to neutrality, dried over MgSO$_4$ and concentrated under vacuum. The solid obtained is reprecipitated from dichloromethane and then purified by silica chromatography (eluent: dichloromethane/ethyl acetate; v/v: 30/70). The compound 8 is obtained in the form of a white solid (1.4 g; melting point of 61.2–62.4° C.; yield of 21%). Its analysis by infrared and proton and carbon-13 NMR is as follows.

IR (dispersion in KBr) ν (cm$^{-1}$): 3330, 3080, 2917, 2849, 1643.
$^1$H NMR (CDCl$_3$, δ (ppm)): 6.0–5.7 (m, 1H), 5.1–4.7 (m, 2H), 3.75–3.65 (m, 2H), 3.55–3.4 (m, 4H), 2.2–1.9 (m, 2H) and 1.7–1.0 (m, 37H, including 1H exchangeable with D$_2$O).
$^{13}$C NMR (CDCl$_3$, δ (ppm)): 139.2, 113.8, 71.7 (2 CH$_2$), 63.7, 33.6–25.8 (19 CH$_2$).

Synthesis of the Unsaturated Alcohol Protected in the Ester Form 9

The unsaturated alcohol 8 (0.9 g, 2.7 mmol) is suspended in dichloromethane (10 ml) and triethylamine (0.6 ml, 5.4 mmol, 2 eq) in a 100 ml two-necked round-bottomed flask. The reaction medium is cooled to 0° C. and then acetyl chloride (0.5 ml, 4 mmol, 1.5 eq) is added dropwise using a syringe. The reaction medium is stirred for 15 minutes at 0° C. and then for 1 h 30 at ambient temperature. It is subsequently hydrolyzed and then extracted three times with diethyl ether. The ethereal phases are combined and washed with a 10% hydrochloric acid solution, with water and then with a saturated NaHCO$_3$ solution. The ethereal phase is then washed to neutrality, dried over MgSO$_4$ and concentrated under vacuum. The compound 9 is obtained in the form of a white solid (0.9 g; yield of 100%). Its analysis by infrared and proton and carbon-13 NMR is as follows.

IR (dispersion in KBr) ν (cm$^{-1}$): 3080, 2917, 2849, 1742, 1643.
$^1$H NMR (CDCl$_3$, δ (ppm)): 6.0–5.7 (m, 1H), 5.1–4.7 (m, 2H), 4.25–4.15 (m, 2H), 3.60–3.50 (t, 2H), 3.45–3.35 (t, 2H), 2.2–1.9 (m, 5H) and 1.7–1.0 (m, 36H).
$^{13}$C NMR (CDCl$_3$, δ (ppm)): 172.0, 139.2, 113.8, 71.5, 68.5, 63.7, 33.6–25.8 (19 CH$_2$), 21.0

3) Introduction of Three Ethylene Glycol Units (FIG. 2)

Starting from the unsaturated iodinated derivative 7 obtained above and from triethylene glycol, an unsaturated alcohol 10 is obtained and is then esterified to produce the product 11, this being carried out according to the same protocols as set out above.

The analysis of the product 10 by infrared and proton and carbon-13 NMR is as follows.

IR (dispersion in KBr) ν (cm$^{-1}$): 3380, 3079, 2919, 2850, 1641.
$^1$H NMR (CDCl$_3$, δ (ppm)): 5.9–5.7 (m, 1H), 5.1–4.7 (m, 2H), 4.3–4.2 (t, 2H), 3.7–3.4 (m, 10H), 3.4–3.3 (t, 2H), 2.2–1.9 (m, 2H) and 1.7–1.0 (m, 37H, including 1H exchangeable with D$_2$O).
$^{13}$C NMR (CDCl$_3$, δ (ppm)): 139.3, 114.0, 71.6–68.2 (6 CH$_2$); 63.6, 33.6–25.8 (19 CH$_2$).

The analysis of the product 11 by infrared and proton and carbon-13 NMR is as follows.

IR (dispersion in KBr) ν (cm$^{-1}$): 3079, 2919, 2850, 1740, 1641.
$^1$H NMR (CDCl$_3$, δ (ppm)): 5.9–5.7 (m, 1H), 5.1–4.7 (m, 2H), 4.3–4.2 (t, 2H), 3.7–3.4 (m, 10H), 3.4–3.3 (t, 2H), 2.2–1.9 (m, 5H) and 1.7–1.0 (m, 36H).
$^{13}$C NMR (CDCl$_3$, δ (ppm)): 171.5, 139.3, 114.0, 71.6–68.3 (6 CH$_2$), 63.6, 33.6–25.8 (19 CH$_2$), 21.0.

Figure 3:
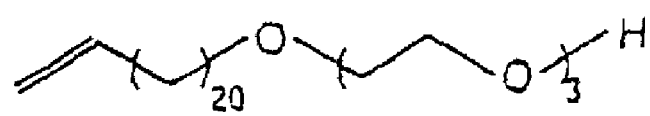
Figure 3:
Figure 3:
Figure 3:
Figure 3:

4) Preparation of the Unsaturated Esters (FIG. 3)

Starting from the unsaturated alcohol 10 obtained above, the corresponding acid and the corresponding ester were prepared as follows.

Preparation of the Acid 12

The unsaturated alcohol 10 (3 g, 6.6 mmol) is suspended in 10 ml acetone in a 100 ml three-necked round-bottomed flask. 5 ml of 2M Jones reagent (Bowden et al., *J. Chem. Soc.*, 1946, 39) are added to the suspension. The suspension is brought to reflux for 2 hours. After returning to ambient temperature, the acetone is evaporated and the solid is filtered off and then rinsed 5 times with water and 3 times with acetone cooled to 0° C. The solid is subsequently purified by recrystallization from a THF/acetone mixture (v/v: 9/1) to give the compound 12 in the form of a white solid (2.9 g; yield of 94%). Its analysis by infrared and proton and carbon-13 NMR is as follows.

IR (dispersion in KBr) ν (cm$^{-1}$): 3370, 3080, 2917, 2849, 1707, 1643.

$^1$H NMR (CDCl$_3$, δ (ppm)): 11.2 (broad s, 1H), 6.0–5.7 (m, 1H), 5.1–4.7 (m, 2H), 4.1–4.0 (s, 2H), 3.6–3.3 (m, 10H), 2.2–1.9 (m, 2H) and 1.7–1.0 (m, 36H).

$^{13}$C NMR (CDCl$_3$, δ (ppm)): 172.1, 139.1, 114.0, 71.6–68.7 (5 CH$_2$), 63.5, 33.6–25.8 (19 CH$_2$).

Preparation of the Ester 13

The acid 12 (2.9 g, 6.4 mmol) is dissolved in anhydrous toluene (7 ml) under an inert atmosphere at 0° C. in a 100 ml three-necked round-bottomed flask. Oxalyl chloride (1.22 g, 9.6 mmol, 1.5 eq) is introduced dropwise and then the mixture is stirred at ambient temperature for 2 hours. The excess reactant and the solvent are subsequently evaporated under vacuum. The acyl chloride is stored temporarily under argon. Methanol (6 ml, 128 mmol, 20 eq), distilled beforehand over calcium chloride, is slowly added. The reaction medium is subsequently brought to reflux for 18 h before being brought back to ambient temperature, and then the excess methanol is evaporated. The reaction medium is then extracted three times with diethyl ether. The ethereal phases are combined and washed with a 10% hydrochloric acid solution, with water and with a saturated NaHCO$_3$ solution. The ethereal phase is subsequently washed to neutrality, dried over MgSO$_4$ and concentrated under vacuum. The compound 13 is obtained in the form of a white solid and is then purified by silica chromatography (eluent: petroleum ether/ether, 50/50 by volume). 300 mg of a white solid are obtained (yield of 10%). Its analysis by infrared and proton and carbon-13 NMR is as follows.

IR (dispersion in KBr) ν (cm$^{-1}$): 3080, 2917, 2849, 1742, 1643.

$^1$H NMR (CDCl$_3$, δ (ppm)): 6.0–5.7 (m, 1H), 5.1–4.7 (m, 2H), 4.1–4.0 (s, 2H), 3.6–3.3 (m, 13H), 2.2–1.9 (m, 2H) and 1.7–1.0 (m, 36H).

$^{13}$C NMR (CDCl$_3$, δ (ppm)): 171.8, 139.1, 114.0, 71.6–68.7 (5 CH$_2$), 63.6, 51.7, 33.6–25.8 (19 CH$_2$).

It is clearly understood that, by using alcohol 8 comprising a single ethylene glycol unit, the corresponding acids and esters could also be obtained according to the same protocols as described here starting from the alcohol 10.

Figure 4:
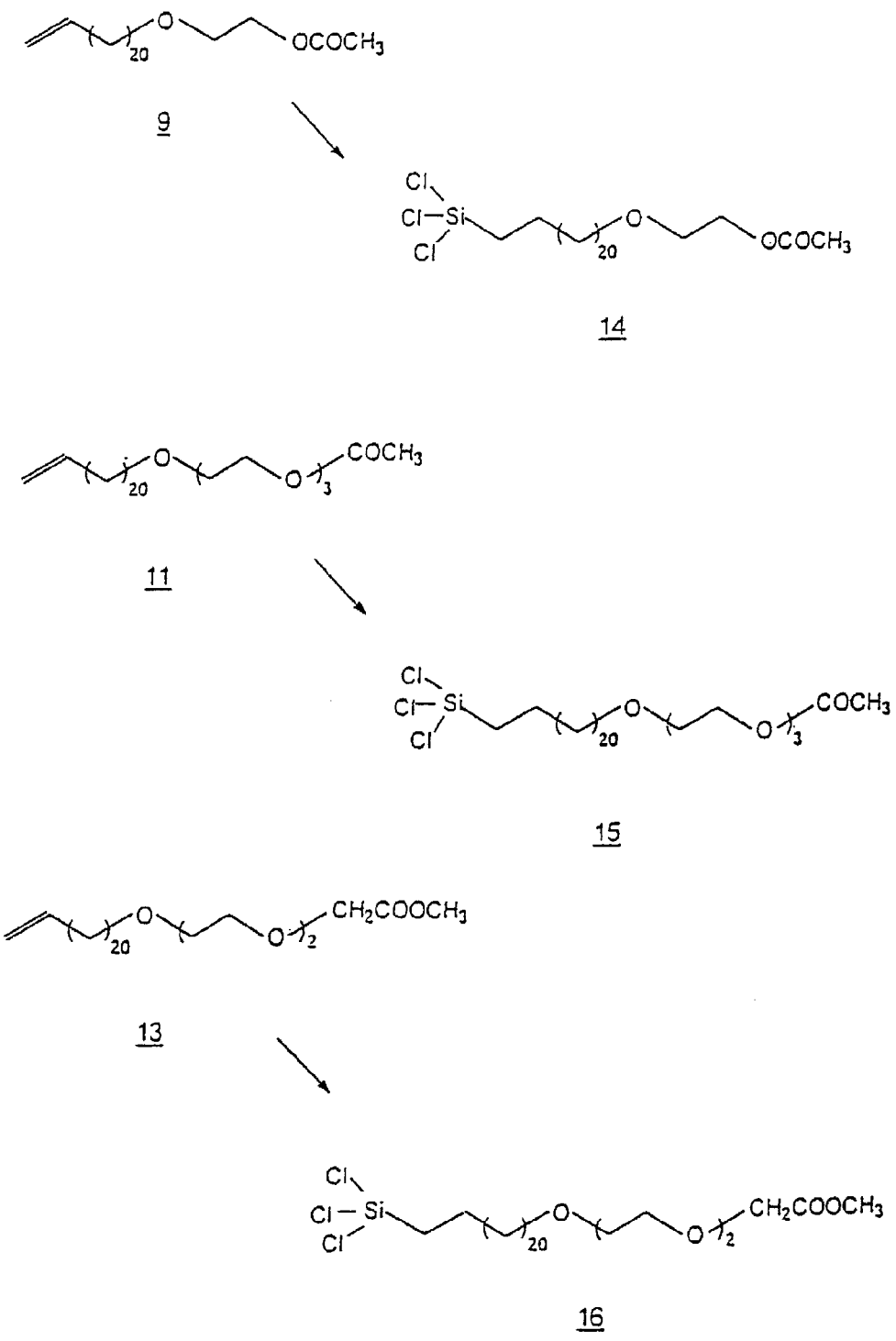
FIG. 4 illustrates the silylation of these unsaturated precursors.

5) Silylation of the Unsaturated Precursors (FIG. 4)

The ester 9 (150 mg, 0.33 mmol) is introduced into a dry Schlenk tube under an inert atmosphere. Freshly distilled trichlorosilane (0.3 ml, 2.2 mmol, 6 eq), anhydrous toluene (0.3 ml) and a dropper Kärsted catalyst (PCO 72), sold by ABCR (reference 68478-92-2), are added. The reaction medium is then cooled to 40° C. for 2 h. After returning to ambient temperature, the toluene and the excess trichlorosilane are evaporated under reduced pressure using a vane pump (pressure is 0.5 mmHg). The compound 14 is obtained in the form of a white solid and is stored under argon (yield at 99%). It is an organosilicon compound of the formula (I) according to the present invention in which X$_1$, X$_2$ and X$_3$ represent chlorine atoms, n is equal to 22, i is equal to 0, k is equal to 1 and Z represents a —COCH$_3$ group.

The analysis of the compound 14 by proton and carbon-13 NMR is as follows.

$^1$H NMR (CDCl$_3$, δ (ppm)): 4.25–4.15 (m, 2H), 3.60–3.50 (t, 2H), 3.45–3.35 (t, 2H), 2.2–1.9 (s, 3H) and 1.7–1.0 (m, 42 H).

$^{13}$C NMR (CDCl$_3$, δ (ppm)): 171.0, 71.5, 68.5, 63.7, 31.9–22.3 (21 CH$_2$), 21.0.

By starting from the compound 11 obtained above and by using the same protocol, the corresponding organosilicon compound 15 is obtained. It is an organosilicon compound of formula (1) according to the present invention in which X$_1$, X$_2$ and X$_3$ represent chlorine atoms, n is equal to 22, i is equal to 0, k is equal to 3 and Z represents the —COCH$_3$ group. Its analysis by proton and carbon-13 NMR is as follows.

$^1$H NMR (CDCl$_3$, δ (ppm)): 4.3–4.2 (t, 2H), 3.7–3.4 (m, 10H), 3.4–3.3 (t, 2H), 2.2–1.9 (s, 3H) and 1.7–0.9 (m, 42H).

$^{13}$C NMR (CDCl$_3$, δ (ppm)): 171.2, 71.6–68.1 (6 CH$_2$), 63.6, 31.9–22.3 (21 CH$_2$), 21.0.

By starting from the compound 13 obtained above and by using the same protocol, the corresponding organosilicon compound 16 is obtained. It is a compound of formula (I) according to the present invention in which X$_1$, X$_2$ and X$_3$ represent chlorine atoms, n is equal to 22, i is equal to 1, k is equal to 2 and Z represents a —COOCH$_3$ group. Its analysis by proton and carbon-13 NMR is as follows.

$^1$H NMR (CDCl$_3$, δ (ppm)): 4.1–4.0 (s, 2H), 3.6–3.3 (m, 13 H), 1.7–0.9 (m, 42H).

$^{13}$C NMR (CDCl$_3$, δ (ppm)): 171.0, 71.6–63.8 (6 CH$_2$), 51.7, 31.9–22.3 (21 CH$_2$).

EXAMPLE 2

Silanization of a Solid Support Using an Organosilicon Compound of Formula (I) and Production of an Organized Self-Assembled Monolayer 1) Silanization of the Solid Support A surface-oxidized silicon disk is used as substrate. The disk is cleaned according to the following procedure, in order to remove the contaminants from its surface and to hydrate it:

immersion in a freshly prepared chromium(VI)/sulfuric acid mixture (2.5 g of K$_2$Cr$_2$O$_4$; 2.5 ml of distilled water; 50 ml of sulfuric acid) for 10 minutes, under a laminar flow hood equipped with dust filters, the disk is immersed in deionized water and subjected to ultrasound for 20 minutes. This process is repeated twice with durations of exposure to ultrasound of 5 and 2 minutes respectively, under a laminar flow hood equipped with dust filters, the disk is introduced into the silanization reactor in order to be dried, under an inert and filtered atmosphere. The reactor is placed for 45 minutes in an oil bath at 100° C., is then removed from the oil bath and its temperature is brought back to 18° C.

The organosilicon compound 14 obtained in example 1, freshly prepared in the desired amount, under an inert atmosphere, is dissolved in a fraction of a C$_6$H$_{12}$/CCl$_4$/CHCl$_3$ (v/v/v: 80/12/8) mixture. The organosilicon compound 14 in solution is subsequently withdrawn with a syringe and then introduced into a Schlenck tube comprising the remainder of the solvent mixture, the total volume of which has been calculated to produce a silanization solution of appropriate dilution (between 1×10⁻⁵ and 1×10⁻² mol/liter). The solvents were dried beforehand according to procedures known per se.

The salinization solution is introduced, with a syringe, into the reactor and the silicon disk remains immersed in this solution for 16 h.

The silanized disk is withdrawn from the reactor, is then immersed in chloroform (HPLC grade) and is cleaned with ultrasound for 2 minutes. This process is subsequently repeated a second time.

2) Characterization of the Modified Surface

A solid support, the surface of which is modified by the compound 14, was obtained above. The grafting of the organosilicon compounds is monitored by using confocal Raman spectroscopy and infrared spectroscopy.

3) Release of the Surface Hydroxyls

If necessary, the surface hydroxyls can be released by using the following protocol: the silanized disk is immersed in a solution of KOH (0.5M) in a water/ethanol (v/v: 1/1) mixture for 20 minutes. The disk is subsequently cleaned with ultrasound for 5 minutes in demineralized water. This process is repeated once in water and then a second time in chloroform.

4) Characterization of the Surface after Release of the Hydroxyls

Figure 5:
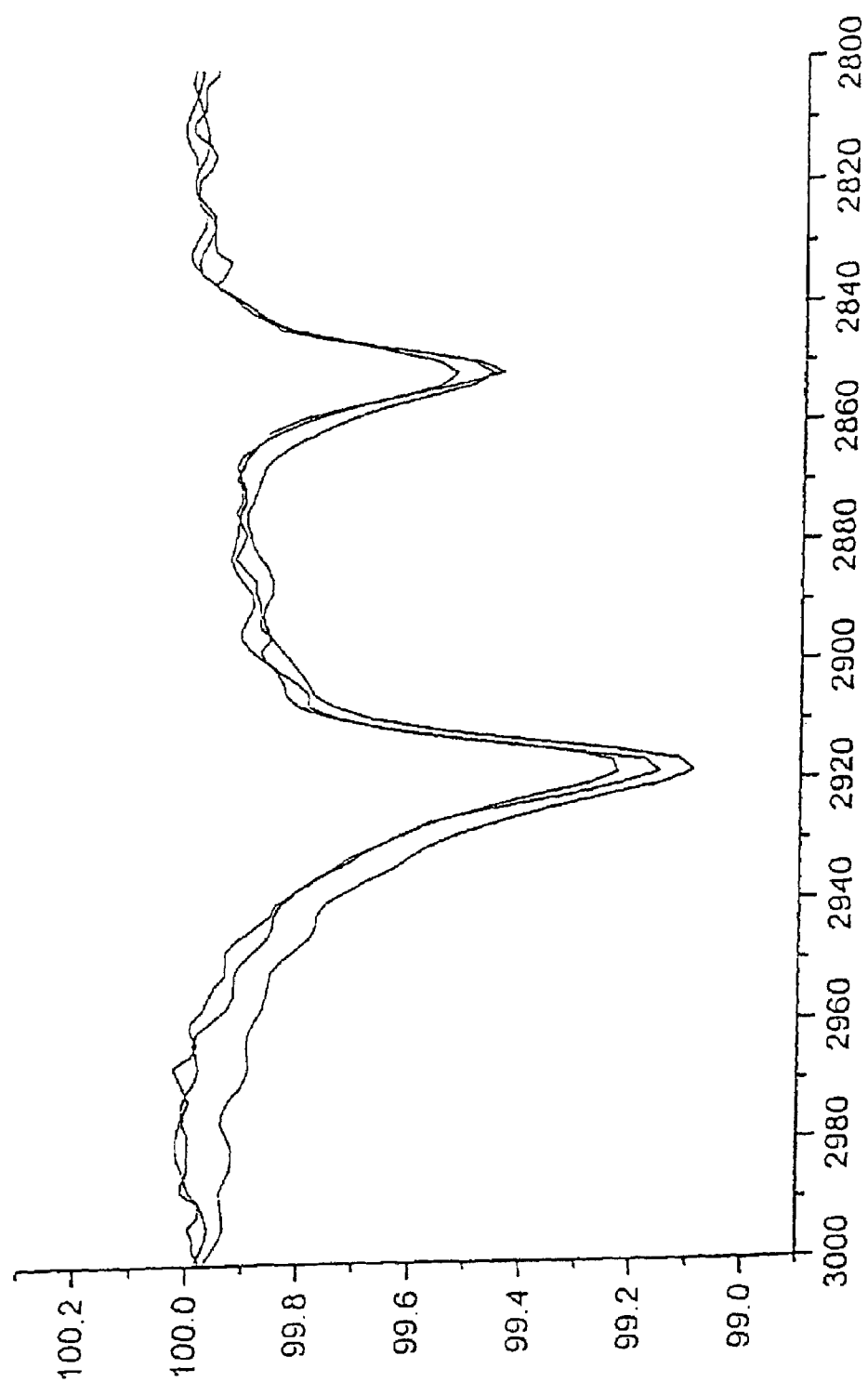
FIG. 5 represents infrared spectra obtained after three experiments of grafting the organosilicon compound 14 to Au/Si/$SiO_2$ substrates.

Infrared spectra obtained after three experiments of grafting the compound 14 to the support according to the protocol given in 1), and after saponification of the surface esters as indicated above, are represented in FIG. 5. The transmission appears on the ordinate and the frequency (cm⁻¹) on the abscissa. It is noted that the three spectra are superimposed, with peaks characteristic of an organized system at 2917 and at 2850 cm⁻¹. Thus, it may be concluded therefrom that the grafting of the organosilicon compound to the support is reproducible and gives rise to the formation of an organized self-assembled monolayer.

Figure 6B:
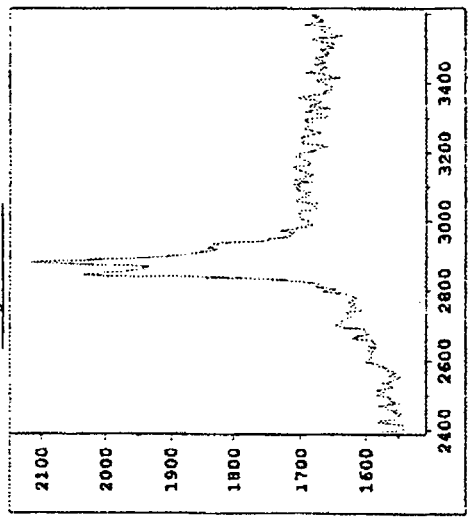
FIGS. 6b and 6c represent the Raman spectra taken at two different points of this surface.
Figure 6C:
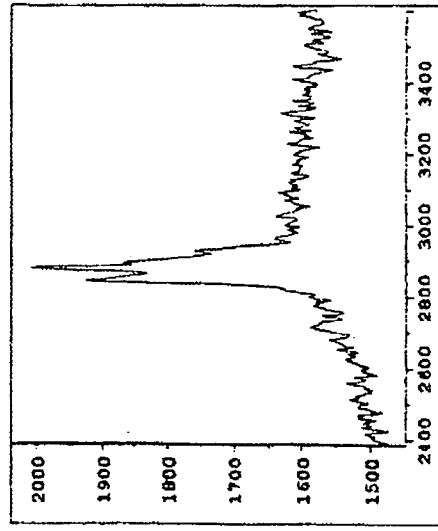
Figure 6A:
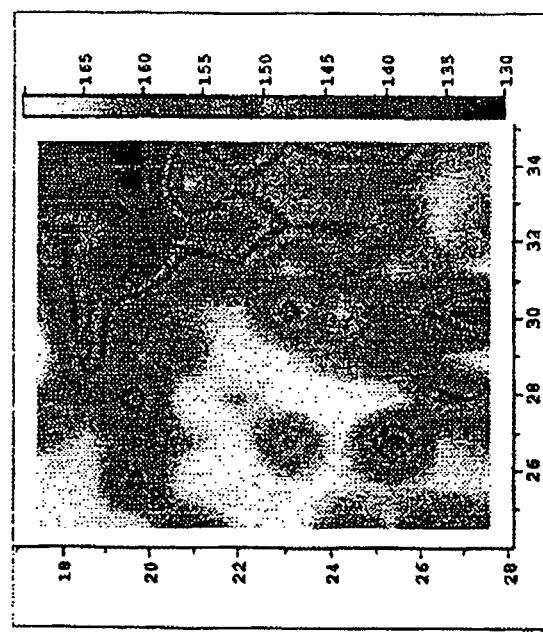
FIG. 6a represents the density, analyzed by Raman spectroscopy, of the surface of the Au/Si/$SiO_2$ substrate to which the organosilicon compounds 14 are grafted.

Raman spectroscopic studies of the modified surface obtained above are represented in FIG. 6. FIG. 6a is representative of the density of the surface of the grafted substrate, the dimensions of the surface appearing on the abscissa and on the ordinate (7 mm in the figure corresponding to 1 μm in the substrate) and the scale of densities being graduated from 130 to 165 (arbitrary units). The homogeneity of the surface is demonstrated by this figure. Raman spectra taken at two different points of the surface of the substrate are represented in FIGS. 6b and 6c; the ordinate represents counts per second and the frequency appears on the abscissa.

Infrared and Raman spectra therefore unambiguously show a homogeneity of the film deposited on the substrate and the organization of the molecules on the surface, characteristic of an organized self-assembled monolayer. The infrared spectrum also shows that the grafting of the film is fully reproducible.

EXAMPLE 3

Other Example of Silanization on a Solid Support Using an Organosilicon Compound of Formula (I)

The glass microscope slide is used as substrate. The glass slide is cleaned by immersion in a 2% aqueous Hellmanex® solution (sold by Polylabo under the reference 12240) for 2 h at 20° C. and then copious rinsing with deionized water.

Under a laminar flow hood equipped with dust filters, the glass slide is introduced into the grafting reactor in order to be dried, under an inert and filtered atmosphere. The reactor is placed for 45 minutes in an oil bath at 100° C., is then removed from the oil bath and its temperature is brought back to 18° C.

The silanization solution, prepared using the organosilicon compound 14 as indicated in example 2, is introduced, with a syringe, into the reactor and the glass slide remains immersed in this solution for 16 h. The silanized substrate is rinsed as described in example 2.

The characterization of the surface by infrared and Raman spectroscopy here again demonstrates the production of an organized self-assembled monolayer on the substrate.

In addition to that which emerges from the above, the invention is in no way restricted to those implementations, embodiments and application forms which have just been described more explicitly; on the contrary, it embraces all the alternative forms thereof which can come to the mind of a technologist in the subject, without departing from the context or from the scope of the present invention.

The invention claimed is:

1. An organosilicon compound of formula (I)

$$X_2-\underset{X_3}{\overset{X_1}{Si}}-(\phantom{}\phantom{})_n O-(\phantom{}\phantom{})-O-\hspace{-0.5em})_k(CH_2)_i-Z \qquad (I)$$

in which:
   n is between 20 and 25,
   k is between 0 and 100,
   i is an integer greater than or equal to 0,
   $X_1$, $X_2$ and $X_3$, which can be identical to or different from one another, are selected from the group consisting of saturated, linear or branched, $C_1$ to $C_6$ alkyls and hydrolyzable groups, at least one from $X_1$, $X_2$ or $X_3$ representing a hydrolyzable group, and
   if k=0 and i=0, then Z represents an $R_1$ group,
   if k=0 and i≧1, then Z represents an —$OR_1$, —$OCOR_1$, —$NR_1R_2$, —$COOR_1$, —$CONR_1R_2$ or —$SR_1$ group or a halogen atom,
   if k≧1 and i=0, then Z represents an —$R_1$, —$COR_1$, —$COOR_1$, —$CONR_1R_2$, —$CF_3$ or —$(CF_2)_jCF_3$ group, j being between 1 and 10,
   if k≧1 and i≧1, then Z represents an —$OR_1$, —$OCOR_1$, —$NR_1R_2$, —$COOR_1$, —$CONR_1R_2$, —$SR_1$, —$CF_3$ or —$(CF_2)_jCF_3$ group, j being as defined above, or a halogen atom,
   $R_1$ and $R_2$, which can be identical or different, represent a hydrogen atom, an optionally substituted, saturated or unsaturated and linear or branched hydrocarbonaceous chain comprising from 1 to 24 carbon atoms, or an aromatic group;
   with the provisos that said organosilicon compound is other than a compound wherein:
   a) $X_1$, $X_2$ and $X_3$ represent chlorine atoms, n is equal to 22, i is equal to 0, k is equal to 1 or to 3, and Z represents a —$COCH_3$ group, or
   b) $X_1$, $X_2$ and $X_3$ represent chlorine atoms, n is equal to 22, i is equal to 1, k is equal to 2, and Z represents a —$COOCH_3$ group.

2. The compound as claimed in claim 1, characterized in that said hydrolyzable group is selected from the group consisting of halogen atoms, the —$N(CH_3)_2$ group and —OR groups, R being a saturated, linear or branched, $C_1$ to $C_6$ alkyl group.

3. The compound as claimed in claim 1, characterized in that k is between 0 and 5.

4. The compound as claimed in claim 1, characterized in that i is equal to 0 or to 1.

5. A process for the preparation of the compound of formula (I) as claimed in claim 1 in which i is other than 1, which comprises the following stages:

a) preparation of an unsaturated precursor of formula (III)

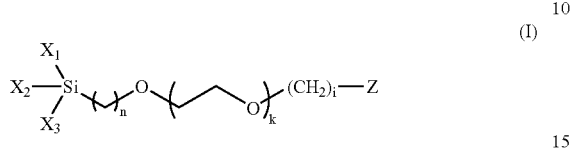

by reaction of a diol of formula $HO-(CH_2-CH_2-O)_k-H$ with an unsaturated compound of formula (II):

in which Y represents a nucleofugal group and n and k are as defined in any one of claims 1 to 4;

b) production, by functionalization of the hydroxyl end of the compound of formula (III), of an unsaturated precursor of formula (IV):

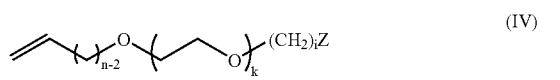

in which Z and i are as defined in any one of claims 1 to 4;

c) production, by hydrosilylation of the unsaturated precursor of formula (IV) using a hydrosilane of formula $HSiX_1X_2X_3$, of a silicon compound of formula (I):

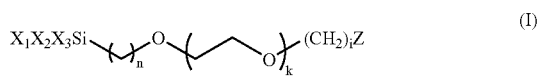

in which at least one from $X_1$, $X_2$ and $X_3$ represents a halogen atom; and d) optionally, production of another compound of formula (I) by substitution of one or more of the $X_1$, $X_2$ and $X_3$ groups of the compound obtained in stage c) using $X_1$, $X_2$ and/or $X_3$ groups as defined in any one of claims 1 to 4.

6. A process for the preparation of the compound of formula (I) as claimed in claim 1 in which i is equal to 1, which comprises the following stages:

a) preparation of an unsaturated precursor of formula (III'):

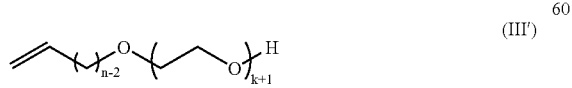

by reaction with a diol of formula $HO-(CH_2-CH_2-O)_{k+1}-H$ with an unsaturated compound of formula (II):

in which Y represents a nucleofugale group and n and k are as defined in claim 1;

b) production, by oxidation of the hydroxyl end of the compound (III'), of an unsaturated precursor of formula (IV'):

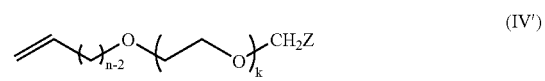

in which Z represents a carboxylic acid functional group;

c) optionally, functionalization of the carboxylic acid end of the compound of formula (IV') using another Z group as defined in claim 1;

d) production, by hydrosilylation of the unsaturated precursor of formula (IV') using a hydrosilane of formula $HSiX_1X_2X_3$, of a silicon compound of formula (I):

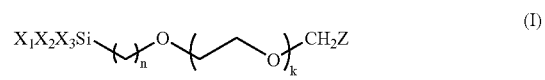

in which at least one from $X_1$, $X_2$ and $X_3$ represents a halogen atom; and e) optionally, production of another compound of formula (I) by substitution of one or more of the $X_1$, $X_2$ and $X_3$ groups of the compound obtained in stage d) using $X_1$, $X_2$ and/or $X_3$ groups as defined in claim 1.

7. A solid support, the surface of which is modified by an organized self-assembled monolayer, characterized in that said monolayer comprises a network of at least one organosilicon compound of formula (I'):

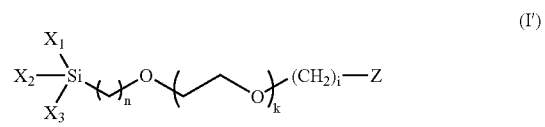

in which:
n is between 20 and 25,
k is between 0 and 100,
i is an integer greater than or equal to 0,
$X_1$, $X_2$ and $X_3$, which can be identical to or different from one another, are selected from the group consisting of saturated, linear or branched, $C_1$ to $C_6$ alkyls and hydrolyzable groups, at least one from $X_1$, $X_2$ or $X_3$ representing a hydrolyzable group, and
if k=0 and i=0, then Z represents an $R_1$ group,
if k=0 and i≧1, then Z represents an $-OR_1$, $-OCOR_1$, $-NR_1R_2$, $-COOR_1$, $-CONR_1R_2$ or $-S\ R$; group or a halogen atom,
if k≧1 and i=0, then Z represents an $-R_1$, $-COR_1$, $-COOR_1$, $-CONR_1R_2$, $-CF_3$ or $-(CF_2)_jCF_3$ group, j being between 1 and 10,
if k≧1 and i≧1, then Z represents an $-OR_1$, $-OCOR_1$, $-NR_1R_2$, $-COOR_1$, $-CONR_1R_2$, —SR$_1$, —CF$_3$ or —(CF$_2$)$_j$CF$_3$ group, j being as defined above, or a halogen atom, R$_1$ and R$_2$, which can be identical or different, represent a hydrogen atom, an optionally substituted, saturated or unsaturated and linear or branched hydrocarbonaceous chain comprising from 1 to 24 carbon atoms, or an aromatic group with the provisos that said organosilicon compound is other than a compound wherein:
a) X$_1$, X$_2$ and X$_3$ represent chlorine atoms, n is equal to 22, i is equal to 0, k is equal to 1 or to 3, and Z represents a —COCH$_3$ group, or
b) X$_1$, X$_2$ and X$_3$ represent chlorine atoms, n is equal to 22, i is equal to 1, k is equal to 2, and Z represents a —COOCH$_3$ group.

8. The support as claimed in claim 7, characterized in that said solid support is such that its surface exhibits, before being modified, hydroxyl groups.

9. The support as claimed in claim 8, characterized in that said solid support is selected from the group consisting of glasses, ceramics, metals and semimetals.

10. A process for the production of the solid support as claimed in claim 7, characterized in that it comprises the following stages:
a) removal of contaminants from a solid support and hydration and/or hydroxylation of its surface,
b) introduction, under an inert atmosphere, of at least one organosilicon compound of formula (I') as defined in claim 7 into a mixture of at least two solvents comprising at least one nonpolar hydrocarbonaceous solvent,
c) silanization of the support obtained in stage a) by immersion in the solution prepared in stage b), and
d) rinsing of the modified support obtained in stage c) using a solvent.

11. The process as claimed in claim 10, characterized in that stage a) is carried out, according to the nature of the solid support, using one or more solvents and/or oxidizing agents and/or hydroxylating agents, a detergent or a photochemical treatment with ozone.

12. The process as claimed in claim 10, characterized in that stage b) is carried out in a mixture of at least one nonpolar hydrocarbonaceous solvent and at least one polar solvent.

13. The process as claimed in claim 12, characterized in that the proportions by volume of nonpolar solvent and of polar solvent are between 70/30 and 95/5.

14. The process as claimed in claim 10, characterized in that the concentration of the organosilicon compound in the mixture of solvents in stage b) of the process is between $1\times10^{-5}$ and $1\times10^{-2}$ mol/liter.

15. A process for the synthesis of biomolecules on the solid support as claimed in claim 7, characterized in that said biomolecules are composed of a sequence of repeat units and in that said process comprises successive stages of grafting said repeat units, the first grafted repeat unit carrying a functional group which is reactive with respect to the Z groups of the organosilicon compounds present on the solid support.

16. A process for the immobilization of biomolecules on the solid support as claimed in claim 7, characterized in that it comprises a stage of grafting said biomolecules, which carry functional groups which are reactive with respect to the Z groups of the organosilicon compounds, to said solid support.

17. The process as claimed in claim 15, characterized in that it is preceded, in the case where the Z end functional group of the organosilicon compounds is an —OCOR$_1$ group in which R$_1$ is as defined in claim 7 or a —COOR$_1$ group in which R$_1$ is as defined in claim 7 and is other than a hydrogen atom, by a stage of deprotection of the corresponding alcohol or carboxylic acid functional group by an appropriate chemical treatment.

* * * * *